US010327851B2

(12) United States Patent
Zoabi et al.

(10) Patent No.: US 10,327,851 B2
(45) Date of Patent: Jun. 25, 2019

(54) METHOD AND APPARATUS FOR ABLATION PLANNING AND CONTROL

(71) Applicant: BIOSENSE WEBSTER (ISRAEL) LTD., Yokneam (IL)

(72) Inventors: Akram Zoabi, Kfar Masser (IL); Fady Massarwi, Baka Al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 197 days.

(21) Appl. No.: 15/376,785

(22) Filed: Dec. 13, 2016

(65) Prior Publication Data
US 2018/0161097 A1 Jun. 14, 2018

(51) Int. Cl.
| | |
|---|---|
| *G06K 9/00* | (2006.01) |
| *A61B 34/10* | (2016.01) |
| *G05B 15/02* | (2006.01) |
| *G06T 7/00* | (2017.01) |
| *G06T 17/00* | (2006.01) |
| *G06T 7/11* | (2017.01) |
| *G16H 50/50* | (2018.01) |

(Continued)

(52) U.S. Cl.
CPC .............. *A61B 34/10* (2016.02); *G05B 15/02* (2013.01); *G06T 7/0012* (2013.01); *G06T 7/11* (2017.01); *G06T 17/00* (2013.01); *G16H 50/50* (2018.01); *A61B 18/1492* (2013.01); *A61B 2018/00351* (2013.01); *A61B 2018/00375* (2013.01); *A61B 2018/00386* (2013.01); *A61B 2018/00577* (2013.01); *A61B 2018/00642* (2013.01); *A61B 2034/104* (2016.02); *A61B 2034/105* (2016.02); *A61B 2034/107* (2016.02); *A61B 2034/2051* (2016.02); *G06T 2207/30004* (2013.01)

(58) Field of Classification Search
CPC ................ A61B 34/10; A61B 18/1492; A61B 2034/104; A61B 2034/107; A61B 2018/00577; G16H 50/50
USPC .......................................................... 382/128
See application file for complete search history.

(56) References Cited

U.S. PATENT DOCUMENTS

| | | | |
|---|---|---|---|
| 5,391,199 A | 2/1995 | Ben-Haim | |
| 6,239,724 B1 | 5/2001 | Doron et al. | |

(Continued)

FOREIGN PATENT DOCUMENTS

| | | | |
|---|---|---|---|
| EP | 2 248 480 A1 | 11/2010 | |
| EP | 2 338 419 A1 | 6/2011 | |

(Continued)

OTHER PUBLICATIONS

European Search Report dated Mar. 5, 2018 from corresponding European Patent Application No. 17206246.5.

(Continued)

*Primary Examiner* — Van D Huynh
(74) *Attorney, Agent, or Firm* — Vincent J. Serrao

(57) ABSTRACT

A method for visualizing ablation includes displaying to a user a three-dimensional (3D) tube that visually represents a region for ablation in tissue of a patient. Ablation information, which specifies one or more ablation locations along the 3D tube and one or more respective ablation configurations for ablating in the ablation locations, is received from the user. An estimated impact of the ablation in the tissue is displayed to the user on the 3D tube based on the ablation locations and the corresponding ablation configurations.

18 Claims, 2 Drawing Sheets

(51) Int. Cl.
  *A61B 18/14* (2006.01)
  *A61B 18/00* (2006.01)
  *A61B 34/20* (2016.01)

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 8,750,568 B2 * | 6/2014 | Frank .................. G06K 9/3216 |
| | | 382/103 |
| 9,265,434 B2 | 2/2016 | Merschon et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2010/0312095 A1 * | 12/2010 | Jenkins ................ A61B 5/415 |
| | | 600/411 |
| 2011/0015628 A1 * | 1/2011 | Dalal ................ A61B 18/1477 |
| | | 606/34 |
| 2011/0152684 A1 | 6/2011 | Altmann et al. |
| 2012/0237105 A1 | 9/2012 | Mielekamp |
| 2012/0277763 A1 | 11/2012 | Greenblatt et al. |
| 2014/0058387 A1 * | 2/2014 | Kruecker ............. A61B 18/148 |
| | | 606/41 |
| 2015/0018698 A1 | 1/2015 | Safran et al. |
| 2016/0183824 A1 | 6/2016 | Severino |
| 2017/0209218 A1 * | 7/2017 | Sahay ................... A61B 6/032 |

FOREIGN PATENT DOCUMENTS

| | | | |
|---|---|---|---|
| WO | WO 2016/181317 A2 | 11/2016 | |
| WO | WO 2016181317 A2 * | 11/2016 | ........... A61B 5/0538 |
| WO | WO-2016181317 A2 * | 11/2016 | ........... A61B 5/0538 |

OTHER PUBLICATIONS

Ranjan R. et al., "Gaps in the Ablation Line as a Potential Cause of Recovery From Electrical Isolation and Their Visualization Using MRI", Circulation, Arrhythmia and Electrophysiology, Jun. 1, 2011, pp. 279-286, vol. 4, No. 3.

* cited by examiner

METHOD AND APPARATUS FOR ABLATION PLANNING AND CONTROL

FIELD OF THE INVENTION

The present invention relates generally to treating arrhythmia, and particularly to methods and apparatus for ablation planning and control.

BACKGROUND OF THE INVENTION

Tissue ablation may be used for treating various types of diseases, such as cardiac arrhythmia. In some cases, the ablation to be applied is complex and requires pre-planning. Various techniques may be applied for planning and controlling the ablation procedure.

For example, U.S. Patent Application Publication 2014/0058387, whose disclosure is incorporated herein by reference, describes a system and method for ablation planning including defining shapes and sizes for one or more ablation volumes based on probability of treatment, and determining a target volume to be treated. A procedure plan is provided by determining a number and location of planned ablations within the target volume using the one or more ablation volumes. A joint probability distribution is determined for at least two planned ablations in the target volume. A final configuration is visualized to determine if plan objectives are met based on a probability of treatment for the target volume.

U.S. Patent Application Publication 2012/0277763, whose disclosure is incorporated herein by reference, describes an interventional ablation therapy planning system, and an imaging system that generates an image representation of a target volume located in a patient. The planning system includes a segmentation unit that segments a planned target volume of the target volume that is to receive the ablation therapy. A planning processor, which generates an ablation plan with one or more ablation zones that cover the entire planned target volume with ablation therapy, each ablation zone has a predetermined ablation volume, the predetermined ablation zone being defined by moving an ablation probe during ablation.

SUMMARY OF THE INVENTION

An embodiment of the present invention that is described herein provides a method for visualizing ablation, including displaying to a user a three-dimensional (3D) tube that visually represents a region for ablation in tissue of a patient. Ablation information, which specifies one or more ablation locations along the 3D tube and one or more respective ablation configurations for ablating in the ablation locations, is received from the user. An estimated impact of the ablation in the tissue is displayed to the user on the 3D tube based on the ablation locations and the corresponding ablation configurations.

In some embodiments, the region is a target region for ablation, and the respective ablation locations and corresponding ablation configurations are planned ablation locations and corresponding planned ablation configurations with which the ablation is planned to be applied. In other embodiments, the respective ablation locations and corresponding ablation configurations are actual ablation locations and corresponding actual ablation configurations used for the ablation. In yet other embodiments, each actual ablation configuration is used for forming a lesion in a respective actual ablation location, and displaying the estimated impact includes evaluating a size and a severity of the lesion at each actual ablation location.

In an embodiment, displaying the estimated impact includes displaying one or more areas along the 3D tube in which neighboring lesions are non-contiguous. In another embodiment, displaying the estimated impact includes displaying one or more areas along the 3D tube in which excess ablation has been applied. In yet another embodiment, displaying the 3D tube includes overlaying the displayed 3D tube on an anatomical image of the tissue at the ablation locations.

In some embodiments, the region includes a pulmonary vein (PV). In other embodiments, the ablation configurations include one or more ablation attributes selected from a list consisting of ablation duration, ablation power, ablation index, target temperature, and impedance drop.

There is additionally provided, in accordance with an embodiment of the present invention, an apparatus for visualizing ablation. The apparatus includes an output device and a processor. The processor is configured to display to a user, on the output device, a three-dimensional (3D) tube that visually represents a region for ablation in tissue of a patient, to receive from the user ablation information that specifies one or more ablation locations along the 3D tube and one or more respective ablation configurations for ablating in the ablation locations, and to display to the user, on the 3D tube, an estimated impact of the ablation in the tissue, based on the ablation locations and the corresponding ablation configurations.

The present invention will be more fully understood from the following detailed description of the embodiments thereof, taken together with the drawings in which:

DETAILED DESCRIPTION OF EMBODIMENTS

Overview

Figure 1:
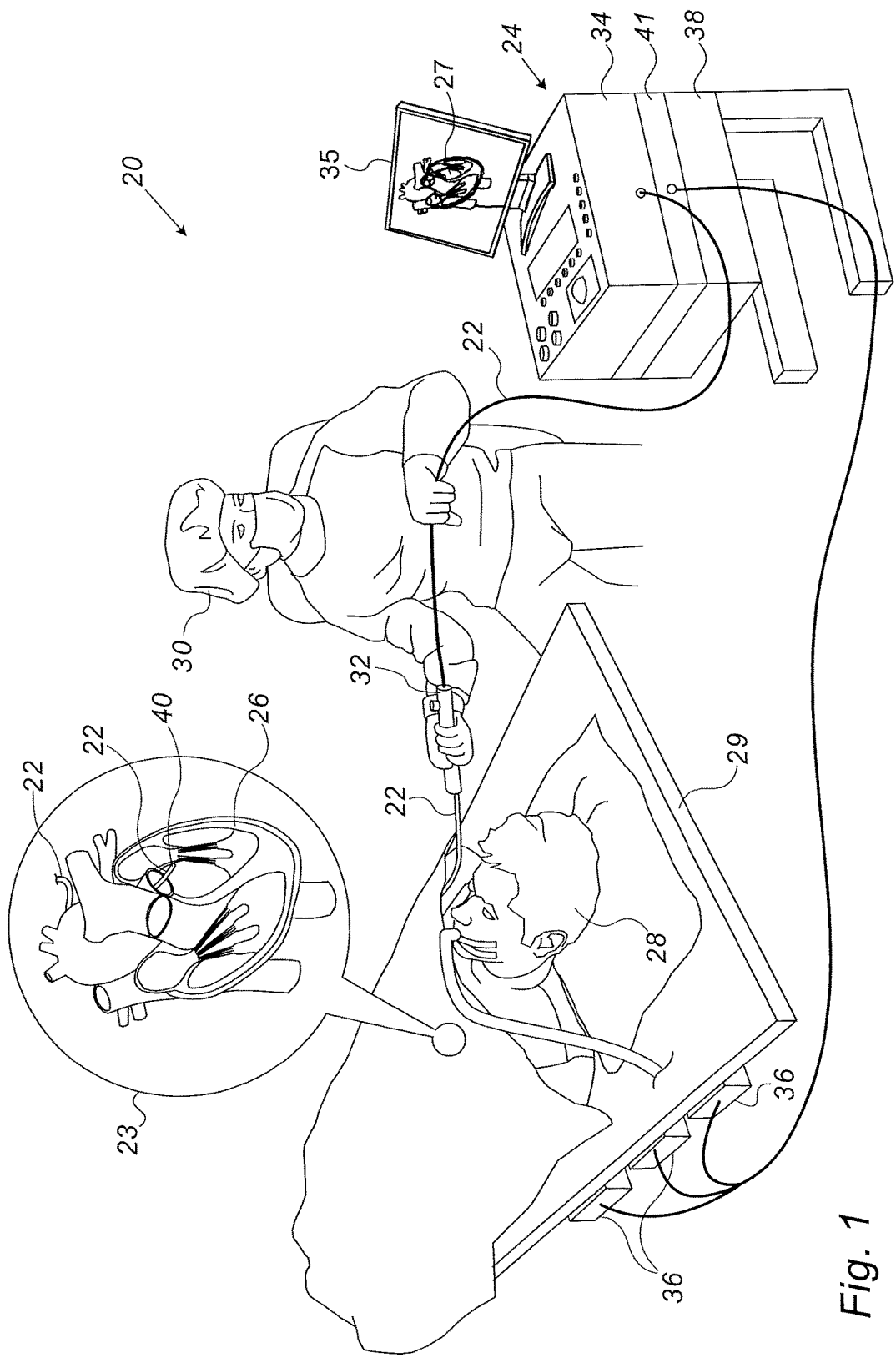
FIG. 1 is a schematic, pictorial illustration of a catheter-based tracking and ablation system, in accordance with an embodiment of the present invention.

Cardiac ablation procedures typically require pre-planning for achieving accurate results. For example, a pulmonary vein (PV) isolation procedure blocks the propagation of undesired electrical impulses across the PV, by ablating a contiguous lesion around the perimeter of the PV. It is important to plan and control the procedure so as to form the contiguous lesion accurately.

Embodiments of the present invention that are described hereinbelow provide improved techniques for planning and controlling ablation procedures. In some embodiments, in planning the ablation procedure, a processor is configured to display to a user (typically a physician) a three-dimensional (3D) tube that visually represents a target region of the PV to be ablated. The user then provides the processor with ablation information that specifies one or more planned ablation locations along the 3D tube, and one or more respective planned ablation configurations for ablating at the specified ablation locations. An ablation configuration for a certain ablation location may specify, for example, the ablation intensity, ablation duration and/or other attributes.

In an embodiment, after receiving the ablation locations and configurations from the user, the processor is configured to activate electrodes of a catheter to ablate the tissue at the ablation locations using the respective ablation configurations, and to display on the 3D tube an estimated impact of the ablation based on actual ablation locations and corresponding actual ablation configurations.

In some cases, one or more of the actual ablation locations and/or the respective actual ablation configurations may differ from the planned ablation locations and/or configurations. In such cases, the processor is configured to display on the 3D tube the difference between the planned and the actual estimated impact of the ablation on the tissue. In some embodiments, the processor is further configured to evaluate the estimated impact of the actual ablation, and to display the evaluation results to the user.

In an embodiment, the processor may detect a discontinuity in the lesion, during planning or during the actual procedure. In this embodiment, the processor may alert the user accordingly and may further suggest modified ablation locations and/or modified configurations so as to fill the discontinuity in the lesion, thereby increasing the probability of forming a contiguous lesion.

The disclosed techniques can be used with various ablating techniques, such as single-electrode ("point-by-point") catheters that ablate one target location at a time, or multi-electrode catheters (e.g., lasso or basket catheters) that ablate multiple target locations simultaneously.

The disclosed techniques provide real-time visualization of the ablation status and enable the physician to plan the ablation and track its progress, so as to immediately correct any deviation from the ablation plan, for example by displaying an undesirable gap between adjacent lesions as an unmarked section of the 3D tube.

Moreover, the disclosed techniques are not limited to cardiac ablation. For example, the disclosed techniques may be used for ablating a tumor, in which case the displayed 3D tube may represent the tumor, with or without safety margins around the tumor.

System Description

FIG. 1 is a schematic, pictorial illustration of a catheter-based tracking and ablation system 20, in accordance with an embodiment of the present invention. System 20 comprises a catheter 22, in the present example a cardiac catheter, and a control console 24. In the embodiment described herein, catheter 22 may be used for any suitable therapeutic and/or diagnostic purposes, such as ablation of tissue (shown in FIG. 2 below) in a heart 26.

Console 24 comprises a processor 41, typically a general-purpose computer, with suitable front end and interface circuits 38 for receiving signals via catheter 22 and for controlling the other components of system 20 described herein. Console 24 further comprises a user display 35, which is configured to display a three-dimensional (3D) tube shown in FIGS. 2 and 3 below that may be overlaid on an image 27 of heart 26.

Figure 2:
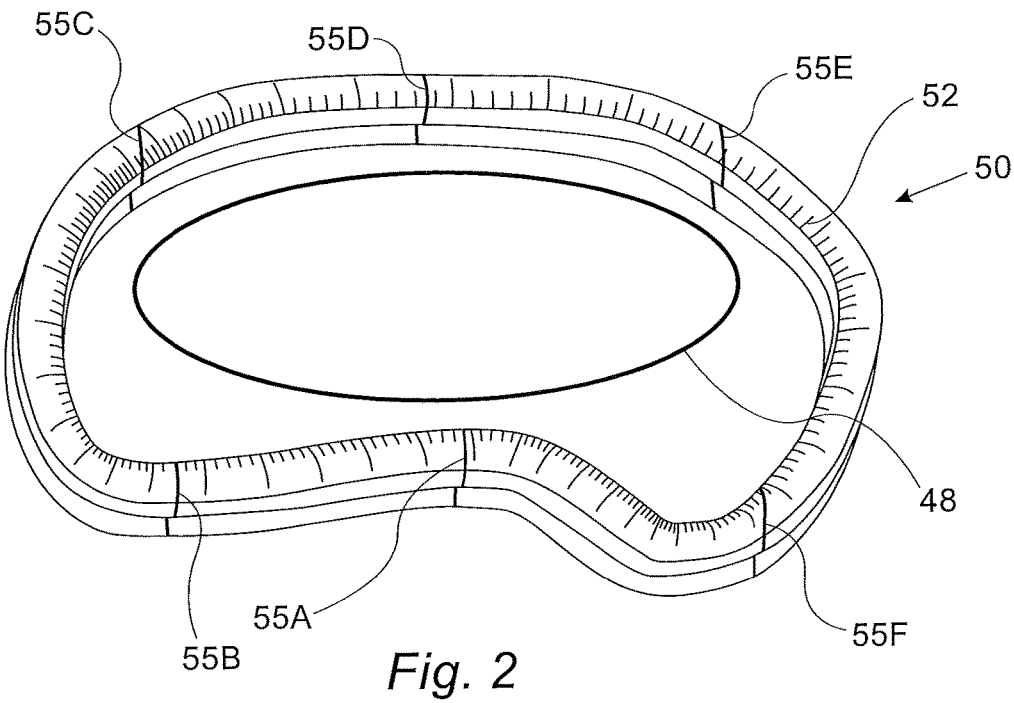
FIG. 2 is a schematic, pictorial illustration of a three-dimensional (3D) tube that visually represents a target region for ablation, in accordance with an embodiment of the present invention.

In an embodiment, the displayed 3D tube may visually represent an estimated impact of the planned locations and corresponding configurations of the ablation before conducting the ablation procedure (as shown in FIG. 2 below). In another embodiment, the displayed 3D tube may represent the estimated impact of the ablation in the tissue based on the actual ablation locations and the corresponding actual ablation configurations. In an embodiment, the 3D tube may be displayed overlaid on image 27 of heart 26.

In some procedures, such as ablation of the tissue, a physician 30 may plan the procedure in advance. In some embodiments, for planning the ablation, processor 41 receives from physician 30 a target region for ablation in the tissue and displays on display 35 a virtual three-dimensional (3D) tube (shown in FIG. 2 below) that visually represents the target region for ablating the tissue of heart 26. The 3D tube is depicted in detail in FIGS. 2-3 below. The physician then provides the processor with the required ablation locations and respective ablation configurations.

To perform the ablation procedure, physician 30 inserts catheter 22 through the vascular system of a patient 28 lying on a table 29. Catheter 22 comprises one or more ablation electrodes 40 fitted at its distal end. Electrodes 40 are configured to ablate tissue at the target location of heart 26. Physician 30 navigates the distal end in the vicinity of the target location in heart 26 by manipulating catheter 22 with a manipulator 32 near the proximal end of the catheter as shown in an inset 23. The proximal end of catheter 22 is connected to interface circuitry in processor 41.

In some embodiments, the position of the distal end in the heart cavity is measured by a position sensor (not shown) of a magnetic position tracking system. In this case, console 24 comprises a driver circuit 34, which drives magnetic field generators 36 placed at known positions external to patient 28 lying on table 29, e.g., below the patient's torso. The position sensor is fitted to the distal end, and configured to generate position signals in response to sensed external magnetic fields from field generators 36. The position signals are indicative of the position the distal end in the coordinate system of the position tracking system.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, physician 30 may use processor 41 for navigating distal end 40 to a target location and for activating electrodes 40 so as to ablate the tissue at the target location. In alternative embodiments, processor 41 may be used only for displaying the 3D tube, and console 22 may comprise one or more other processors that may be used for the navigation of distal end 40 and for the ablation of the tissue.

Processor 41, typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Planning the Ablation Procedure

FIG. 2 is a schematic, pictorial illustration of a virtual three-dimensional (3D) tube 50 that visually represents a target region for ablation, as displayed to physician 30 on display 35, in accordance with an embodiment of the present invention. In the example of FIG. 2, the ablation procedure aims to isolate a pulmonary vein (PV) 48 of heart 26, but the embodiments described herein may be used in any other ablation procedure.

In the planning stage of the procedure, one or more anatomical images of PV 48 are displayed to physician 30 on display 35. The anatomical images may be acquired using any suitable imaging technique, such as echocardiography, multi-detector computerized tomography (MDCT), or fast anatomical mapping (FAM) implemented, for example, in the CARTO™ system, produced by Biosense Webster Inc. (Diamond Bar, Calif.) and is described in detail in U.S. Pat. No. 9,265,434, in U.S. Patent Application Publications 2011/0152684 A1, 2015/0018698 A1 and 2016/0183824 A1, and in European patent application publication EP2338419 A1, whose disclosures are all incorporated herein by reference.

In an embodiment, as part of the planning phase, physician 30 selects multiple ablation locations and corresponding ablation configurations, and provides this information to processor 41. In an embodiment, physician 30 may set a specific ablation configuration at every ablation location. In some embodiments, the ablation configuration may specify various ablation attributes, such as ablation duration, ablation power, ablation index, target temperature, impedance drop, or any other suitable ablation attribute. In the present example, six ablation locations denoted 55A, 55B, 55C, 55D, 55E, and 55F have been selected. Processor 41 uses the image of PV 48, as well as the target ablation locations and ablation configurations specified by physician to display virtual 3D tube 50 on display 35.

In some embodiments, processor 41 is configured to estimate, for each ablation location, the size of the lesion that would be formed assuming the respective ablation configuration were applied. In an embodiment, processor 41 is configured to mark a colored section of tube 50 on either side of the ablation location. The size of these colored sections corresponds to the estimated size of the lesion.

In some embodiments, this technique may be used in the ablation planning stage, in which case physician 30 may start with an initial ablation plan of locations and corresponding ablation configurations. In an embodiment, processor 41 displays the estimated impact of the planned ablation by filling the respective sections of tube 50 accordingly.

By using this visualization technique, physician 30 can plan the procedure adaptively, e.g., in a way that will fill the entire tube, thereby ensuring formation of a contiguous lesion. In case the estimated ablation impact indicates that the planned scheme does not form a contiguous lesion, processor 41 will display unmarked (e.g., transparent) sections in tube 50 that are indicative of a non-contiguous lesion. In such cases, physician 30 may modify the planned scheme, e.g., by moving ablation locations along tube 50, adding or removing locations, and/or modifying the ablation configurations in one or more ablation locations. Processor 41 will display the estimated impact of the modified plan on tube 50 for reevaluation. Physician 30 may repeat this iterative plan modification process until the medical requirements are fulfilled.

In some embodiments, the processor displays tube 50 with a scale 52 to assist physician 30 in selecting the ablation locations along tube 50. The physician provides the processor with a respective ablation configuration for each selected ablation location. Locations 55A-55F are virtually displayed e.g., as marks, on tube 50.

In some embodiments, processor 41 is configured to mark on tube 50 the expected lesion boundaries at each selected ablation location, based on the respective ablation configuration, for assisting physician 30 in planning and execution of the ablation procedure. For example, using the boundaries marks physician 30 may modify the ablation configurations for achieving a contiguous lesion around PV 48.

In an embodiment, processor 41 is further configured to display tube 50 overlaid on the anatomical image of PV 48 as shown in FIG. 2, or on any anatomical reconstruction of an organ selected by physician 30. In other embodiments, tube 50 may be presented separately.

Displaying Estimated Impact of the Ablation

Figure 3:
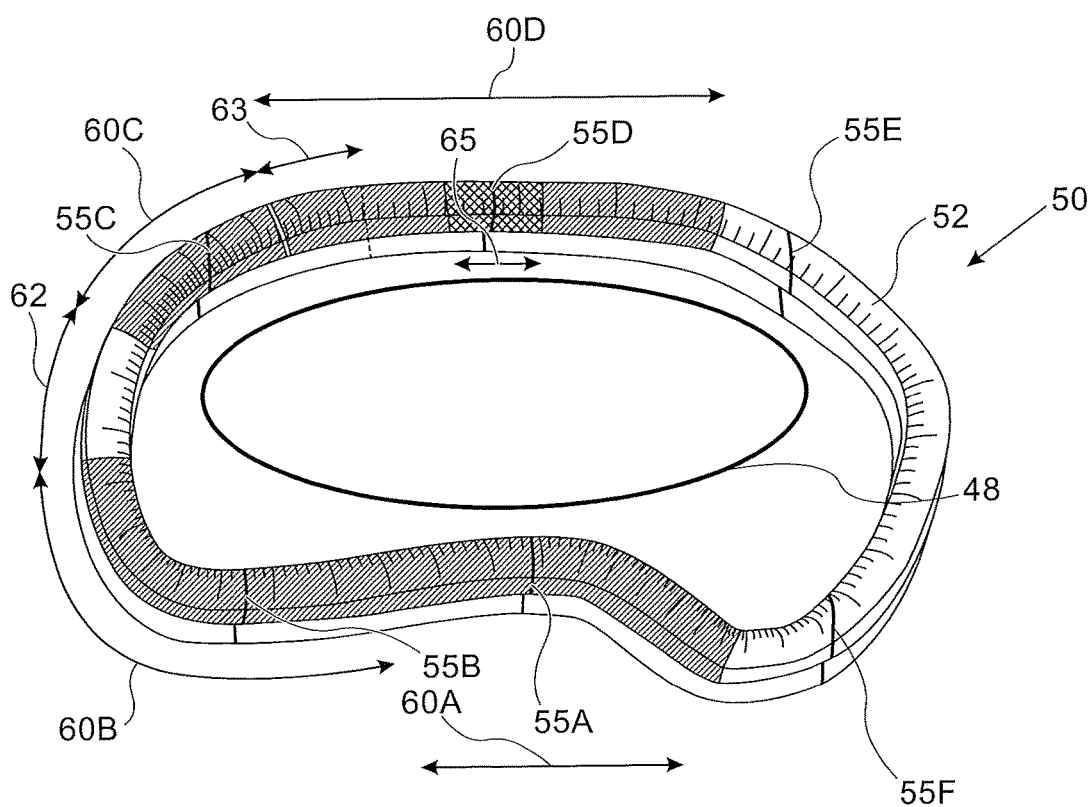
FIG. 3 is a schematic, pictorial illustration of a 3D tube that visually represents an estimated impact of ablation in tissue, in accordance with an embodiment of the present invention.

FIG. 3 is a schematic, visual illustration of an estimated impact of the ablation using virtual 3D tube 50, in accordance with an embodiment of the present invention.

In an embodiment, during the ablation procedure, processor 41 receives the position of the distal end from the position sensor fitted thereon, and displays the position of ablation electrodes 40 with respect to tube 50 so that physician 30 may navigate the distal end to the selected ablation locations (e.g., location 55A). After navigating the distal end, e.g., to location 55A, physician 30 activates electrodes 40 for ablating the tissue using the predefined ablation configuration of location 55A, as described in FIG. 2 above.

Typically, the ablation is carried out at the planned locations and using the respective planed configurations. In some cases, however, the actual ablation applied to the tissue may deviate from the planned ablation. For example, during the ablation of the tissue, the actual ablation configuration may differ from the planned configuration. As another example, the actual position of distal end 40 may deviate from the exact planned location. In such cases, the resulting lesion will not match the exact lesion as planned.

After ablating at location 55A, processor 41 virtually "fills" a section 60A of tube 50 with color that represents the actual lesion formed by the ablation. In an embodiment, processor 41 displays the filled color in section 60A based on the actual location of distal end during the ablation ("actual ablation location" as obtained from the position tracking system) and based on the actual ablation configuration performed at this location.

In an embodiment, the size and the color of section 60A (measured along scale 52) visualize the actual impact of the ablation on the tissue at location 55A. In some embodiments, physician 30 may use the size and color of section 60A to estimate the actual ablation impact relative to the ablation plan and to adjust the ablation configuration at location 55B, which is the next planned ablation location.

In the example of FIG. 3, the ablations at locations 55A and 55B fills the planned section of tube 50 as shown by respective sections 60A and 60B. In this example, the visualization of the ablation impact at location 55C, as shown by a section 60C, covers less than the planned area, as demonstrated by sections 62 and 63 that remain transparent in tube 50. Transparent section 62 indicates that a contiguous lesion was not formed in this section, and therefore, this discontinuity may fail to block propagation of undesired electrical impulses across PV 48.

In some embodiments, processor 41 may suggest a modified ablation configuration, or physician 30 may manually modify the ablation configuration at location 55D so as to form a contiguous lesion in section 63, that is required for blocking undesired electrical impulses from passing through section 63. For example, at location 55D physician 30 may increase the actual ablation power and/or extend the actual ablation duration so as to close the gap of section 63 and to form a contiguous lesion visualized by sections 60C and 60D.

In an embodiment, processor 41 is further configured to display abnormal estimated ablation impact. For example, processor 41 may display, at a section 65, excess ablation caused, for example, by modifying the ablation configuration at location 55D. The excess ablation may be displayed using a predetermined color, texture, or any other suitable visualization effect that indicates the actual impact of the excess ablation on the tissue.

In some embodiments, processor 41 may suggest an ablation strategy (e.g., an ablation location and a corresponding ablation configuration) for filling section so as to complete the formation of the contiguous lesion around PV 48.

In some embodiments, after concluding the ablation at locations 55A-55F, processor 41 may evaluate the ablation impact along tube 50. For example, processor 41 may evaluate whether the ablation has actually formed a contiguous lesion, and notify physician 30 in case of identified discontinuity or any other unexpected outcome of the ablation along tube 50.

In some embodiments, processor 41 is further configured to display the distance between the location of distal end 40 and one or more of the planned ablation locations.

The configuration of tube 50 and the corresponding ablation scheme shown in FIGS. 2-3 are example configurations that are shown purely for the sake of conceptual clarity. In alternative embodiments, any other suitable configuration can be used. For example, the virtual 3D tube may have a linear shape so as to form an ablation line.

In the embodiments described herein, processor 41 visualizes tube 50 in a two-phase process—First during planning and then during the actual ablation procedure. In alternative embodiments, the disclosed techniques can be used only during planning, or only during the actual procedure.

Although the embodiments described herein mainly address cardiology, the methods and systems described herein can also be used in other applications, such as in tumor ablation.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A computer implemented method for visualizing ablation, the method comprising:
generating in a processor, a three-dimensional (3D) tube having a toroidal shape, the 3D tube visually representing a region for ablation in tissue of a patient;
displaying to a user on a display device operatively connected to the processor the 3D tube;
receiving from an input device operatively connected to the processor, user input ablation information that specifies one or more ablation locations along the 3D tube, and one or more respective ablation configurations for ablating in the ablation locations;
calculating an estimated impact of ablation, including boundaries of an estimated ablation lesion size assuming the respective one or more ablation configurations were applied to the one or more ablation locations along the 3D tube; and
displaying to the user on the display device, the 3D tube updated to visually show the estimated impact of the ablation in the tissue based on the one or more ablation locations and the corresponding one or more ablation configurations.

2. The method according to claim 1, wherein the region is a target region for ablation, and wherein the respective ablation locations and corresponding ablation configurations are planned ablation locations and corresponding planned ablation configurations with which the ablation is planned to be applied.

3. The method according to claim 1, wherein the respective ablation locations and corresponding ablation configurations are actual ablation locations and corresponding actual ablation configurations used for the ablation.

4. The method according to claim 3, wherein each actual ablation configuration is used for forming a lesion in a respective actual ablation location, and wherein displaying the estimated impact comprises evaluating a size and a severity of the lesion at each actual ablation location.

5. The method according to claim 4, wherein displaying the estimated impact comprises displaying one or more areas along the 3D tube in which neighboring lesions are non-contiguous.

6. The method according to claim 4, wherein displaying the estimated impact comprises displaying one or more areas along the 3D tube in which excess ablation has been applied.

7. The method according to claim 1, wherein displaying the 3D tube comprises overlaying the displayed 3D tube on an anatomical image of the tissue at the ablation locations.

8. The method according to claim 1, wherein the region comprises a pulmonary vein (PV).

9. The method according to claim 1, wherein the ablation configurations comprise one or more ablation attributes selected from a list consisting of ablation duration, ablation power, ablation index, target temperature, and impedance drop.

10. Apparatus for visualizing ablation, the apparatus comprising:
an output device;
an input device; and
a processor operatively connected to the output device and the input device, the processor being configured to generated a three-dimensional (3D) tube having a toroidal shape that visually represents a region for ablation in tissue of a patient, to display to a user on the output device the 3D tube, to receive from the user through the input device ablation information that specifies one or more ablation locations along the 3D tube and one or more respective ablation configurations for ablating in the ablation locations, to calculate an estimated impact of ablation, including boundaries of an estimated ablation lesion size assuming the respective one or more ablation configurations were applied to the one or more ablation locations along the 3D tube, and to display to the user via the output device, the 3D tube, updated to visually show the estimated impact of the ablation in the tissue based on the one or more ablation locations and the corresponding one or more ablation configurations.

11. The apparatus according to claim 10, wherein the region is a target region for ablation, and wherein the respective ablation locations and corresponding ablation configurations are planned ablation locations and corresponding planned ablation configurations with which the ablation is planned to be applied.

12. The apparatus according to claim 10, wherein the respective ablation locations and corresponding ablation configurations are actual ablation locations and corresponding actual ablation configurations used for the ablation.

13. The apparatus according to claim 12, wherein each actual ablation configuration is used for forming a lesion in a respective actual ablation location, and wherein the processor is configured to evaluate a size and a severity of the lesion at each actual ablation location.

14. The apparatus according to claim 13, wherein the processor is configured to display one or more areas along the 3D tube in which neighboring lesions are non-contiguous.

15. The apparatus according to claim 13, wherein the processor is configured to display one or more areas along the 3D tube in which excess ablation has been applied.

16. The apparatus according to claim 10, wherein the processor is configured to overlay the displayed 3D tube on an anatomical image of the tissue at the ablation locations.

17. The apparatus according to claim 10, wherein the region comprises a pulmonary vein (PV).

18. The apparatus according to claim 10, wherein the ablation configurations comprise one or more ablation attributes selected from a list consisting of ablation duration, ablation power, ablation index, target temperature, and impedance drop.

* * * * *